United States Patent [19]

Anderson et al.

[11] Patent Number: 4,904,662
[45] Date of Patent: Feb. 27, 1990

[54] RAISING OF PIGS

[75] Inventors: David B. Anderson; Edward L. Veenhuizen, both of Greenfield, Ind.

[73] Assignee: Eli Lilly and Company, Indianapolis, Ind.

[21] Appl. No.: 29,024

[22] Filed: Mar. 23, 1987

Related U.S. Application Data

[63] Continuation-in-part of Ser. No. 901,908, Aug. 28, 1986, abandoned, which is a continuation-in-part of Ser. No. 802,541, Nov. 27, 1985, abandoned.

[51] Int. Cl.$^4$ ............... A61K 31/535; A61K 31/275; A61K 31/16
[52] U.S. Cl. ................... 514/237.8; 514/524; 514/616; 514/629; 514/630; 514/653
[58] Field of Search ............... 514/653, 524, 616, 629, 514/630, 237.8

[56] References Cited

U.S. PATENT DOCUMENTS

| | | | |
|---|---|---|---|
| 3,994,974 | 11/1976 | Murakami et al. | 266/562 |
| 4,391,826 | 7/1983 | Mills et al. | 424/309 |
| 4,407,819 | 10/1983 | Kiernan et al. | 424/272 |
| 4,432,995 | 2/1984 | Kiernan et al. | 424/465 |
| 4,614,746 | 9/1986 | Asato et al. | 514/524 |

FOREIGN PATENT DOCUMENTS

| | | |
|---|---|---|
| 0117647 | 5/1984 | European Pat. Off. |
| 57-10864 | 3/1982 | Japan |
| WO86/05075 | 9/1986 | PCT Int'l Appl. |

OTHER PUBLICATIONS

Moser & Lewis, *Feed Stuffs*, 3/3/80, Adding Fat to Sow Diets–An Update.
Jim Pettigrew, *J. An. Sci.*, 53, 107-17 (1981).
D. E. Bauman & C. L. Davis, *Lactation*, vol. II, Biosynthesis of Milk Fat, pp. 26 & 31-75 (1974).
*C. A.* 84, 58894v (1976).
*Derwent*, 10229x (1976).

*Primary Examiner*—Frederick E. Waddell
*Attorney, Agent, or Firm*—Donald R. Stuart; Joseph A. Jones; Leroy Whitaker

[57] ABSTRACT

The fat content of sows' milk is increased, thereby increasing the energy supplied to the sow's piglets, by administering one of a small group of phenethanolamines.

20 Claims, No Drawings

RAISING OF PIGS

CROSS-REFERENCE

This application is a continuation-in-part of copending application Ser. No. 901,908, filed Aug. 28, 1986, now abandoned which is a continuation-in-part of then copending application Ser. No. 802,541, filed Nov. 27, 1985, now abandoned.

BACKGROUND OF THE INVENTION

Baby pigs are born in particularly weak and defenseless condition. Their skin and hair are thin and fragile, compared to the young of other economic animals, and their reserves of stored nutrients are very low. In particular, the fat reserves of a piglet are very slight.

Thus, piglets deplete their glycogen reserves very soon after birth. If an individual piglet is slow to suckle or gets less than its share of colostrum and milk, it will very soon be in desperate condition. The observed result is that only about 75% of piglets survive to adulthood.

It has been found that the survival of piglets can be measurably improved by expedients which raise the fat content of sows' colostrum and milk. For example, Moser and Lewis reported in Feedstuffs, Mar. 3, 1980, that the addition of fats to the diet of lactating sows increased the fat content of their colostrum and milk, and resulted in an increase of about 2.6% in the survival of their piglets, compared to normally-fed controls.

The addition of fats to animal feeds, however, is rather difficult. The physical mixing involved is much more difficult than the simple mixing of grain and cereal products involved in ordinary feeds, and the resulting fat-containing feed is difficult to measure, transport and store. The amounts of fat necessary to produce the desired effect add appreciably to the cost of sows' feed, as well. Until now, there has been no physiological way to increase fat content of sows' colostrum and milk.

The present invention provides a method of increasing the fat concentration of sows' colostrum and milk, by administering one of a small group of phenethanolamines. The phenethanolamines constitute a very large and complex group of pharmaceuticals, useful in both human and veterinary medicine. Various members of the broad class of phenethanolamines have many diverse activities, and accordingly can be used for a number of pharmacological purposes.

For example, European patent publication No. 0117647, of Anderson et al., teaches that a group of phenethanolamines, including some of those used in the present invention, can be effectively administered to animals to improve feed efficiency and carcass quality. The patent mention pigs as a preferred animal, and states that use of its compounds causes the treated animal to be lean, as compared to untreated animals. U.S. Pat. Nos. 4,407,819 and 4,432,995, of Kiernan et al., teach that other compounds used in the present invention increase lean meat deposition and the lean to fat ratio, as well as feed efficiency and growth rate, in animals, including swine.

It has been established that the only lipid fraction of blood which is taken up in significant and consistent quantity by the sow's mammary gland is the triglyceride fraction. *Lactation*, Larsen and Smith, Eds., Vol. II, p. 26 (Academic Press, 1974).

Some phenethanolamines have been shown in the past to release fat deposits in the body, in the form of free fatty acids. For example, the above-mentioned European patent application states at page 31 that its compounds, when administered to normal swine, increased the concentration of non-esterified fatty acids in the blood, compared to untreated control animals.

Another class of phenethanolamines, which are specified extremely precisely in terms of their stereochemistry, is taught by U.S. Pat. No. 4,391,826, of Mills et al. These compounds are said to be useful as anti-obesity agents. The patent shows at the top of column 13 that administration of typical compounds to rats caused a great increase in the concentration of free fatty acids in the blood.

SUMMARY OF THE INVENTION

The present invention provides a method of increasing the fat content of the colostrum or milk of a lactating sow which comprises administering to said sow, at a time from about 3 days before farrowing to about 10 days after farrowing, a milk-fat-increasing amount of a compound of the formula

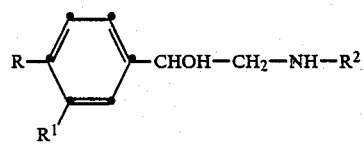

wherein:
R is hydrogen, hydroxy, methoxy or amino;
$R^1$ is hydrogen, cyano or $NR^3R^4$;
$R^3$ is hydrogen or methyl;
$R^4$ is hydrogen, methyl, formyl or —COCH$_2$NHCHO;
$R^2$ is $C_2$–$C_4$ alkyl or

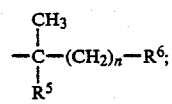

$R^5$ is hydrogen or methyl;
n is 1 or 2;
$R^6$ is morpholino or

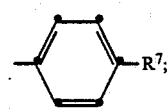

$R^7$ is hydrogen, hydroxy, fluoro, nitro, carbamoyl or methoxy;
provided that:
R and $R^7$ are not both hydrogen;
$R^7$ is not hydroxy when R is hydrogen;
R is hydrogen or amino when $R^1$ is cyano;
R is hydrogen, hydroxy or methoxy when $R^1$ is hydrogen;
$R^2$ is not $C_2$–$C_4$ alkyl when $R^1$ is hydrogen;
R is not methoxy when $R^2$ is alkyl, when $R^6$ is morpholino, or when $R^7$ is hydrogen, fluoro, nitro or methoxy;
or a physiologically acceptable acid addition salt thereof.

The compounds used in the present invention are known to the organic chemical and animal husbandry arts. The synthesis of some compounds is taught in European Patent Application No. 84300559.6, published on Sept. 5, 1984 under publication No. 0117647. The same disclosure is in U.S. Patent Application 860,717 filed May 7, 1986. Other compounds are taught by U.S. Pat. Nos. 4,407,819, 4,432,995 and 3,994,974, and Japanese Kokai No. 75-111,036, which is abstracted at C.A. 84, 58894v (1976), and by Derwent at 10229x (1976).

The administration of certain classes of compounds described above is preferred. Each of the following limitations describes a specific class of preferred compounds. It will be understood that the following limitations may be combined to describe further classes of preferred compounds.

(a) R is hydrogen or hydroxy;
(b) R is hydroxy;
R is amino;
$R^1$ is hydrogen;
(e) $R^1$ is cyano;
(f) $R^1$ is formylamino or methylamino;
(g) $R^1$ is $NR^3R^4$;
(h) $R^2$ is $C_2$–$C_4$ alkyl;
(i) $R^2$ is

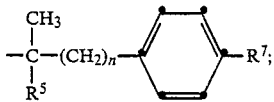

(j) $R^2$ is isopropyl or t-butyl;
(k) $R^2$ is secondary or tertiary;
(l) $R^3$ is hydrogen;
(m) $R^5$ is hydrogen;
(n) $R^6$ is morpholino;
(o) $R^7$ is hydroxy, methoxy, fluoro, nitro or carbamoyl;
(p) $R^7$ is hydroxy, methoxy or carbamoyl.

Another preferred group of compounds includes those of the formula

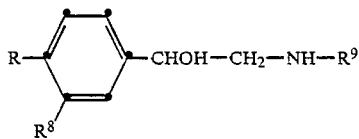

wherein:
$R^8$ is hydrogen or cyano;
$R^9$ is $C_2$–$C_4$ alkyl or

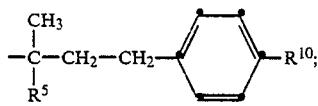

$R^{10}$ is hydrogen, hydroxy, fluoro, nitro or carbamoyl; provided that:
R and $R^{10}$ are not both hydrogen;
$R^{10}$ is not hydroxy when R is hydrogen;
R is hydrogen, hydroxy or methoxy when $R^8$ is hydrogen;
$R^9$ is $C_2$–$C_4$ alkyl when and only when $R^8$ is cyano;
or a physiologically acceptable acid addition salt thereof.

The most preferred individual compounds for use in the invention are the following.
1-(4-hydroxyphenyl)-2-[3-(4-hydroxyphenyl)-1-methylpropylamino]ethanol
2-[3-(4-aminocarbonylphenyl)-1-methylpropylamino]-1-phenylethanol
2-[1-methyl-3-(4-nitrophenyl)propylamino]-1-phenylethanol
1-(4-amino-3-cyanophenyl)-2-isopropylaminoethanol
1-(4-amino-3-cyanophenyl)-2-ethylaminoethanol
1-(3-formamido-4-hydroxyphenyl)-2-[2-(4-methoxyphenyl)-1-methylethylamino]ethanol
1-(3-formamido-4-hydroxyphenyl)-2-(1-methyl-3-morpholinopropylamino)ethanol
2-t-butylamino-1-(4-hydroxy-3-methylaminophenyl)ethanol
1-(3-amino-4-hydroxyphenyl)-2-isopropylaminoethanol
1-(3-formamidoacetamido-4-hydroxyphenyl)-2-[2(4-methoxyphenyl)-1-methylethylamino]ethanol
2-t-butylamino-1-[4-hydroxy-3-(N-methylformamido)-phenyl]ethanol
1-(3-formamidoacetamido-4-hydroxyphenyl)-2--(4-hydroxyphenyl)-1-methylethylamino]ethanol
and the physiologically acceptable salts of the above compounds.

Additional typical compounds for use in the present invention are the following.
2-(1,1-dimethyl-3-phenylpropylamino)-1-(4-hydroxyphenyl)ethanol
2-[3-(4-fluorophenyl)-1-methylpropylamino]-1-phenylethanol
2-[1,1-dimethyl-3-(4-hydroxyphenyl)propylamino]-1-(4-hydroxyphenyl)ethanol
2-[1,1-dimethyl-3-(4-nitrophenyl)propylamino]-1-(4-hydroxyphenyl)ethanol
2-[1,1-dimethyl-3-(4-hydroxyphenyl)propylamino]-1-(4-methoxyphenyl)ethanol
2-[1,1-dimethyl-3-(4-fluorophenyl)propylamino]-1-phenylethanol
2-t-butylamino-1-(4-amino-3-cyanophenyl)ethanol
2-s-butylamino-1-(4-amino-3-cyanophenyl)ethanol
1-(3-cyanophenyl)-2-isopropylaminoethanol Throughout the present document, all expressions of percentage, proportions and the like are in parts by weight.

The compounds for use in the present invention may be advantageously used in the form of salts, and it will be understood that all of the specifically named compounds above may be in the form of physiologically-acceptable salts. Most preferably, the compounds are used in the form of hydrohalide salts, especially as the hydrochlorides. However, any desired physiologically-acceptable salt may be used. For example, such typical salts as sulfates, acetates, formates, fumarates, toluenesulfonates, methanesulfonates, lactates, citrates, napthalenesulfonates, phosphates, succinates and the like may be used as desired.

Organic chemists will immediately recognize that the compounds used in this invention have one or two asymmetric centers. The stereochemistry of the compounds is not indicated above, and it is preferred to use the compounds as the racemic mixtures, containing all of the possible stereoisomers. However, it is recognized that, at some time, it may be advantageous to separate the isomers and to identify and use only the isomer or isomers which provides the greatest effect. Such a separation and identification is an obvious procedure in organic chemistry, and the use of the separated active isomers is contemplated by the present inventors to be an embodiment of the present invention.

TEST 1

The experimental animals were crossbred sows, primarily of Yorkshire extraction, which had previously borne from 1 to 5 litters and which were about to farrow. The sows were kept in farrowing crates, in a concrete block building with concrete slats, and were fed a cornsoy diet containing 10% of beet pulp which provided 16% protein. Each farrowing crate had an individual feeder and automatic waterer, and heat lamps and radiant heat bars were available to warm the piglets as necessary.

Three sows made up the untreated control group, and two sows each were placed in 6 treatment groups. The test compound was dl-1-(4-hydroxyphenyl)-2-[3-(4-hydroxy-phenyl)-1-methylpropylamino]ethanol, hydrochloride. The compound was administered orally to some sows, by pipetting an aqueous solution of the drug on each sow's feed at each of the morning and afternoon feedings. The compound, also as an aqueous solution, was injected subcutaneously in the rear flank area of those sows to which the administration was by injection. Injections were administered at 8 and 11:30 a.m. and at 3:30 p.m.

The treatments were started at 8:00 a.m. the morning after each sow farrowed, and were continued for 3 days. Milk samples were obtained at the time of the morning and afternoon feedings by injecting oxytocin and milking the sows by hand. The milk samples were analyzed to determine fat content by infrared analysis.

The following table reports the results of the milk fat analyses, as averages of the treatment groups. One sow in the 0.1 mg/kg subcutaneous administration group died for reasons unrelated to the test, so the results of that treatment are based on only one sow.

TABLE 1

| Treatment Group | Milk Fat Content |
|---|---|
| Control | 6.36 |
| 0.2 mg/kg, oral, 2× | 7.61% |
| 0.5 mg/kg, oral, 2× | 7.27% |
| 1.0 mg/kg, oral, 2× | 7.06% |
| 0.02 mg/kg, subcutaneous, 3× | 7.17% |
| 0.05 mg/kg, subcutaneous, 3× | 6.53% |
| 0.1 mg/kg, subcutaneous, 3× | 8.72% |

TEST 2

A group of 18 gilts, of crossbred origin, were used in a test substantially like that of Test 1. Six gilts were placed in each of a control group, a group which received the compound of Test 1 orally at the rate of 0.2 mg/kg twice daily in their feed, and in a group which received the same compound at a rate of 0.02 mg/kg subcutaneously, 3 times per day. Administration of the test compounds began on the fourth day after each gilt farrowed.

The animals were fed a corn-soy diet containing 16% crude protein, and were given feed and water ad lib.

The milk fat analyses are reported, as averages of the treatment groups, in the following table.

TABLE 2

| Treatment Group | PERCENT MILK FAT | | |
|---|---|---|---|
| | Day 1 | Day 3 | Day 5 |
| Control | 6.65 | 6.65 | 6.60 |
| Oral | 7.80 | 7.75 | 6.75 |
| Subcutaneous | 7.25 | 7.65 | 7.50 |

In this experiment, 14 sows were assigned to 2 treatment groups, a control group and a group which received 0.02 mg/kg of the compound used in Test 1 in each of 3 daily subcutaneous injections, starting on the day of farrowing. The sows were managed as described in Test 1.

The sows' milk was analyzed, and it was found that the average milk fat content of the control sows' milk was 5.6% over the first 3 days after farrowing. The milk fat content of the sows in the treated group was 7.7%, for the same period of time.

The present invention is carried out by administering a compound of the group described above to a sow which is about to farrow or which has just farrowed. The compounds may be administered either orally, as by mixing the compound in the sow's feed, or percutaneously. Administration should be started not more than three days before the expected farrowing date. Since the whole point of the invention is to provide extra energy to new-born piglets, there is no point in carrying the invention out more than about 10 days after farrowing. Most effectively, administration of a compound of the invention should be started on the day of farrowing and should be continued for from about 3 to about 7 days.

When a compound is to be administered orally, it may be combined with the sow's feed or water, or be administered as a pharmaceutical dosage form such as a drench. It is preferred to administer the compound in the sow's feed.

For such administration, it is convenient and conventional to prepare a feed premix of the compound. A feed premix is a relatively concentrated mixture of the compound in an edible diluent, which is mixed with an appropriate amount of finished feed. Premixes usually are solid particulate mixtures, wherein the compound is diluted with rice hulls, soybean meal, coarsely ground grain or other similar substances. A feed premix may be pelleted to control dust, or the diluent may be a clay, in which case the premix may be granulated according to conventional methods. A typical premix has an active ingredient content in the range of from about 10% to about 80% by weight.

It is possible but unusual to make liquid feed premixes, wherein the compound is dissolved or suspended in an aqueous or organic liquid such as water, propylene glycol and the like.

A compound may, of course, be mixed with a sow's feed without the use of a feed premix, by simply weighing the proper amount of compound for a dose and combining it with a portion of feed which the sow is sure to eat. Such a procedure may be appropriate for the present compounds, since the administration of them continues only for a short time and is begun at a precise time.

Administration of a compound in a sow's water is carried out by preparing a formulation of the compound which can be dissolved or suspended in water, and mixing it in the water supply. For example, a compound may be formulated in a physiologically-acceptable glycol, an aqueous solution of a glycol or an alcohol, and the like.

Finally, a compound may be dissolved or suspended in a physiologically-acceptable diluent and may be administered orally to the sow, as a drench, for example. Such a procedure, however, is not preferred, because of the difficulty of administration.

Further, the compounds of the present invention may be effectively administered percutaneously, as by intramuscular or subcutaneous injection. The preparation of injectable formulations is well understood. In general, it is necessary only to dissolve or suspend the compound in a physiologically-acceptable liquid medium, preferably an aqueous medium such as water, propylene glycol, aqueous ethanol and the like, and to provide appropriate suspending agents as may be needed.

The dosage range of a compound used in the present invention is in the range from about 0.001 to about 2 mg/kg/day, for oral administration, and in the range from about 0.0005 to about 0.5 mg/kg/day, for percutaneous administration. It is preferable to administer the compound in multiple doses through the day, rather than in a single dose. For example, it is most preferred to administer a compound in the sow's feed, and to keep feed available to her at all times, so that she consumes her daily dose in portions throughout the day and night. If the compound is administered percutaneously, similarly, it is preferred to divide the daily dose and administer it in two, three, or four injections.

More specifically, the preferred dosage range of a compound wherein $R^2$ is phenylalkyl is from about 0.05 to about 2 mg/kg/day, for oral administration, and from about 0.005 to about 0.5 mg/kg/day, for percutaneous administration. In the case of compounds wherein $R^2$ is alkyl or morpholino, the preferred oral dosage range is from about 0.001 to about 2 mg/kg/day, and the preferred percutaneous dose range is from about 0.0005 to about 0.5 mg/kg/day.

Most preferably, an oral dose of a compound wherein $R^2$ is phenylalkyl is in the range from about 0.25 to about 1 mg/kg/day, and a percutaneous dose is in the range from about 0.05 to about 0.2 mg/kg/day. The most preferable oral dose range of a compound wherein $R^2$ is alkyl or morpholino is from about 0.025 to about 1 mg/kg/day, and the most preferable percutaneous dose range is from about 0.005 to about 0.2 mg/kg/day.

We claim:

1. A method of increasing the triglyceride content of the colostrum or milk of a lactating sow which comprises administering to said sow, at a time from about 3 days before farrowing to about 10 days after farrowing, a milk-fat-increasing amount of a compound of the formula

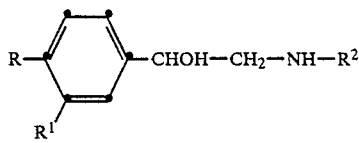

wherein:
R is hydrogen, hydroxy, methoxy or amino;
$R^1$ is hydrogen, cyano or $NR^3R^4$;
$R^3$ is hydrogen or methyl;
$R^4$ is hydrogen, methyl, formyl or —COCH$^2$NHCHO;
$R^2$ is $C_2$–$C_4$ alkyl or

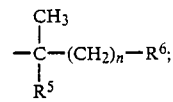

$R^5$ is hydrogen or methyl;
n is 1 or 2;
$R^6$ is morpholino or

$R^7$ is hydrogen, hydroxy, fluoro, nitro, carbamoyl or methoxy;
provided that:
R and $R^7$ are not both hydrogen;
$R^7$ is not hydroxy when R is hydrogen;
R is hydrogen or amino when $R^1$ is cyano;
R is hydrogen, hydroxy or methoxy when $R^1$ is hydrogen;
$R^2$ is not $C_2$–$C_4$ alkyl when $R^1$ is hydrogen;
R is not methoxy when $R^2$ is alkyl, when $R^6$ is morpholino, or when $R^7$ is hydrogen, fluoro, nitro or methoxy;
or a physiologically acceptable acid addition salt thereof.

2. A method of claim 1 wherein the administration is begun on the day of farrowing and continues for from about 3 to about 7 days after farrowing.

3. A method of claim 2 wherein the administration is oral at a dosage rate from about 0.05 to about 2 mg/kg/day.

4. A method of claim 2 wherein the administration is percutaneous at a dosage rate from about 0.005 to about 0.5 mg/kg/day.

5. A method of claim 3 wherein the dosage rate is from about 0.25 to about 1 mg/kg/day.

6. A method of claim 4 wherein the dosage rate is from about 0.05 to about 0.2 mg/kg/day.

7. A method of claim 1 wherein the compound is a compound wherein R is hydrogen or hydroxy.

8. A method of claim 7 wherein $R^7$ is hydroxy or carbamoyl.

9. A method of claim 1 wherein the compound is 1-(4-hydroxyphenyl)-2-[3-(4-hydroxyphenyl)-1-methylpropylamino]ethanol or a physiologically-acceptable acid addition salt thereof.

10. A method of claim 3 wherein the compound is 1-(4-hydroxyphenyl)-2-[3-(4-hydroxyphenyl)-1-methylpropylamino]ethanol or a physiologically-acceptable acid addition salt thereof.

11. A method of claim 4 wherein the compound is 1-(4-hydroxyphenyl)-2-[3-(4-hydroxyphenyl)-1-methylpropylamino]ethanol or a physiologically-acceptable acid addition salt thereof.

12. A method of claim 1 wherein the compound is 2-[3-(4-aminocarbonylphenyl)-1-methylpropylamino]-1-phenylethanol or a physiologically-acceptable acid addition salt thereof.

13. A method of claim 3 wherein the compound is 2-[3-(4-aminocarbonylphenyl)-1-methylpropylamino]-1-phenylethanol or a physiologically-acceptable acid addition salt thereof.

14. A method of claim 4 wherein the compound is 2-[3-(4-aminocarbonylphenyl)-1-methylpropylamino]-1-phenylethanol or a physiologically-acceptable acid addition salt thereof.

15. A method of claim 1 wherein the compound is 1-(4-amino-3-cyanophenyl)-2-isopropylaminoethanol or a physiologically-acceptable acid addition salt thereof.

16. A method of claim 3 wherein the compound is 1-(4-amino-3-cyanophenyl)-2-isopropylaminoethanol or a physiologically-acceptable acid addition salt thereof.

17. A method of claim 4 wherein the compound is 1-(4-amino-3-cyanophenyl)-2-isopropylaminoethanol or a physiologically-acceptable acid addition salt thereof.

18. A method of claim 1 wherein the compound is 1-(3-formamido-4-hydroxyphenyl)-2-[2-(4-methoxyphenyl)-1-methylethylamino]ethanol or a physiologically-acceptable acid addition salt thereof.

19. A method of claim 1 wherein the compound is 1-(3-formamido-4-hydroxyphenyl)-2-(1-methyl-3-morpholinopropylamino)ethanol or a physiologically-acceptable acid addition salt thereof.

20. A method of claim 1 wherein the compound is 2-t-butylamino-1-(4-hydroxy-3-methylaminophenyl)ethanol or a physiologically-acceptable acid addition salt thereof.

* * * * *

UNITED STATES PATENT AND TRADEMARK OFFICE
CERTIFICATE OF CORRECTION

PATENT NO. : 4,904,662
DATED : February 27, 1990
INVENTOR(S) : David B. Anderson et al It is certified that error appears in the above-indentified patent and that said Letters Patent is hereby corrected as shown below:

Column 3, insert after line 63, "R is hydrogen or amino when $R^8$ is cyano."

Column 4, line 23, "-4 hydroxy" should read, -- [2-(4 hydroxy --.

Column 7, line 66, "$COCH^2NH$" should read, -- $COCH_2NH$ --.

Signed and Sealed this

Seventeenth Day of October, 1995

Attest:

BRUCE LEHMAN

Attesting Officer

Commissioner of Patents and Trademarks